(12) United States Patent  
Curtis et al.

(10) Patent No.: US 6,507,638 B2  
(45) Date of Patent: Jan. 14, 2003

(54) X-RAY IMAGING OPTICAL CAMERA APPARATUS AND METHOD OF USE

(75) Inventors: Steven E. Curtis, Salt Lake City, UT (US); R. Larry Anderton, West Jordan, UT (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 9 days.

(21) Appl. No.: 09/867,820

(22) Filed: May 30, 2001

(65) Prior Publication Data

US 2002/0181657 A1 Dec. 5, 2002

(51) Int. Cl.[7] .................................................. H05G 1/64
(52) U.S. Cl. ....................................... 378/98.3; 378/98.7
(58) Field of Search ........................ 378/98, 98.2, 98.3, 378/98.7

(56) References Cited

U.S. PATENT DOCUMENTS 4,749,257 A * 6/1988 Klausz .......................... 349/1
6,226,351 B1 * 5/2001 Snoeren et al. ............ 378/98.12

* cited by examiner

Primary Examiner—David P. Porta
(74) Attorney, Agent, or Firm—McAndrews, Held & Malloy, Ltd.; Peter J. Vogel; Michael A. Dellapenna

(57) ABSTRACT

An electronic video camera apparatus is provided for focusing light rays from object plane proximate image intensifier of a medical x-ray imaging system onto an image plane proximate a light sensor. The electronic video camera includes a lens system located between the object and image planes to focus light rays from the object plane onto the image plane. The light rays at the object plane are representative of a patient image. An optical filter is located between the object and image planes and partially blocks light rays passing there through. The optical filter includes at least first and second filter regions having different opacity. The first and second filter regions are alignable with the lens system at different times to block differing first and second amounts of light rays, respectively, associated with differing first and second x-ray amounts transmitted at different times.

20 Claims, 6 Drawing Sheets

X-RAY IMAGING OPTICAL CAMERA APPARATUS AND METHOD OF USE

BACKGROUND OF THE INVENTION

At least one preferred embodiment of the present invention generally relates to a medical x-ray imaging system employing an electronic video camera that operates upon visible light to control brightness. At least one preferred embodiment of the present invention relates to an electronic video camera that utilizes a neutral density filter having varying opacity across the filter and that is adjustable for light attenuation.

In the past, medical diagnostic imaging systems have been proposed for imaging regions of interest in patients through the use of x-ray sources and receptors positioned on opposite sides of a patient's region of interest. Typical x-ray imaging systems utilize an x-ray source and receptor that are movable to various positions relative to the patient's region of interest. The x-ray source is controlled to adjust the amount of x-rays transmitted therefrom, passed through the patient and impinged on the x-ray receptor. X-ray receptors generally include an image intensifier having an x-ray detection layer that detects x-rays passing through a patient. The image intensifier converts the x-rays to visible light which is, in turn, guided onto an object plane proximate a video camera. The video camera includes an optical lens system focusing light from the object plane onto an image plane proximate a light sensitive sensor. One example of a light sensitive sensor is a charge coupled device. The light sensitive sensor detects and converts the visible light at the image plane data that is processed and ultimately displayed to a user.

Various anatomical regions attenuate x-rays to different degrees depending upon thickness, density, structure and the like of the anatomic region. These different characteristics of patient anatomy attenuate x-rays to different degrees and may degrade x-ray images where an anatomy of interest is located proximate certain other types of anatomy.

Operators of x-ray imaging equipment attempt to improve image quality of x-ray images through a variety of manners. One such manner for improving x-ray image quality involves adjusting the x-ray intensity transmitted by the x-ray source. For instance, anatomical regions that highly attenuate x-rays are imaged better by increasing the number of x-rays transmitted from the source. By increasing the x-ray transmissions, the user similarly increases the photon statistics sensed at the receptor (e.g., the number of photons impingent upon the image intensifier). As the photon statistics increase, the image intensifier converts more and more x-rays to visible light, thereby increasing the brightness of the light incident on the object plane of the electronic video camera. The light brightness may rise to a level sufficient to saturate the light sensor, such as the CCD. As the sensed light becomes excessive, the resulting processed and displayed image degrades. Image degradation may appear in several forms, such as a washed out image, an image having poor contrast between adjacent anatomies, and the like.

In the past, x-ray systems have attempted to prevent the light brightness from overloading the sensor by adding an iris to the electronic video camera having an adjustable opening passing only a desired amount of light. The diameter of the opening can be varied to affect the desired average attenuation of the brightness of the light at the object plane. As the system reduces the iris opening to "stop down" or partially close the iris opening, feedback sensing will detect that the average brightness of the light at the object plane is reduced, and the system can automatically increase the amount of x-rays impinging upon the receptor.

In accordance with the foregoing, the quality of the ultimately displayed image is influenced by the amount of x-ray flux (intensity) that is incident upon the image intensifier. The amount of light that is allowed to pass through the optics of the electronic video camera typically controls the amount of x-ray flux. A higher quality image requires more x-ray flux and more x-ray flux is permitted by decreasing the iris aperture that passes light through the camera optics, thereby avoiding sensor saturation. Motor controlled irises precisely control the amount of light passed through the optics in order to ensure that the minimum x-ray flux necessary is used in view of patient concerns. The iris aperture diameter and thus the amount of x-ray flux may be varied during single patient imaging procedure. Hence, light intensity is typically controlled automatically by the x-ray imaging system in accordance with commands from a user entered to initiate an imaging operation.

It is preferable that the electronic video camera only focus light near the object plane onto the image plane. The compact nature of x-ray systems typically results in the object plane and image plane being in close proximity to opposite ends of the camera optics. Hence, structure within the camera optics, such as glass surfaces and the like through which the light passes are located proximate the object plane. The glass surface and other transparent structure near the object plane may be focused by the camera optics onto the image plane as the iris aperture is reduced. These transparent structures in or near the camera optics may contain blemishes, such as scratches, digs and the like and may accumulate foreign material such as dirt. The blemishes and/or dirt may be close enough to the object plane as to become at least partially focused onto the image plane when the iris aperture is stopped down. The camera optics may partially focus images of the blemishes or dirt onto the image plane sufficiently that the light sensor at the image plane detects the blemishes/dirt as data conveyed to the processor to be imaged. These projections of blemishes and dirt create unwanted artifacts at the image plane that result as artifacts appearing in the displayed image.

FIG. 8 illustrates an exemplary configuration for the camera optics as formed in accordance with conventional systems. The camera optics 75 include a glass or other transparent layer 77 located at the input side to the camera optics proximate the object plane 79. The glass or other transparent layer 77 represents any kind of structure that could be part of the camera optics 75 such that this structure presents an opportunity for its surfaces to contain blemishes or dirt that may partially be in focus. For example, structure 77 could be part of the forward lens system 81, or structure 77 could be leaded glass installed for the purpose of reducing x-ray radiation beyond the optics such as would otherwise irradiate the optical sensor. The image intensifier directs light rays representative of an x-ray image onto the object plane 79. A forward lens system 81 is located proximate the glass layer 77 which directs light ray traces 83 and 86, from the object plane 79 through optical components 87 onto a rear lens system 89. The forward lens system also directs light ray traces 84 and 85 from blemishes/dirt in the glass layer 77 onto the rear lens system 89. The forward lens system 81 collimates the light ray traces 83–86, while the rear lens system 89 reconverges the light ray traces 83–86. The forward and rear lens systems 81 and 89 cooperate such that light ray traces 83 and 86 projecting from the object plane are collimated at the forward lens system 81 into a parallel manner and converged at the rear lens system 89 onto an image plane 91. When blemishes and dirt exist on the surface of the glass layer 77, light ray traces 84 and 85 are focused by the forward and rear lens systems 81 and 89 at a point 97

An adjustable iris 93 is opened and closed based upon the desired x-ray flux to control the amount of light ray traces passed therethrough onto the rear lens system 89. As the adjustable iris 93 reduces the opening therethrough, the shape and size of a focus region 95 proximate the image plane 91 expands. The focus region represents an area in which light rays are adequately in focus to be detectable at the image plane by the light sensor as a distinct image for which data is generated and processed (albeit possibly as an artifact). The size of the focus region 95 is relatively small when the iris 93 is open to a relatively large state. When in a relatively closed state (as illustrated in FIG. 8), the iris 93 forms a relatively large focus region 95 that includes light ray traces 84 and 85 projected from the surface of the glass layer 77. Hence, while the projection of blemishes and dirt are not focused directly on the image plane 91, the point 97 at which such blemishes and dirt are focused is adequately close to the image plane 91 to be sufficiently in focus at the image plane 91 that an artifact is created in the data generated by the light sensor. The partially focused images at the image plane 91 of dirt and other blemishes are detected by the sensor, processed and displayed along with the x-ray image. The image portions associated with the dirt and blemishes appear as artifacts in the resulting x-ray image. Hence, reducing the iris aperture may increase the tendency of dirt or blemishes close to the object plane to manifest themselves on the image plane.

A need remains for an improved x-ray imaging system and electronic video camera apparatus that avoids the disadvantages discussed above, while permitting x-ray flux to be increased when desired to obtain a higher quality image.

BRIEF SUMMARY OF THE INVENTION

In accordance with at least one embodiment of the present invention, in a medical x-ray imaging system, an electronic video camera is provided for focusing light rays from an object plane proximate an image intensifier onto an image plane proximate a light sensor. The electronic video camera includes an object plane receiving light rays representative of a patient image. A lens system is provided between the object plane and image plane to focus the light rays from the object plane onto the image plane. An optical filter is also located between the object and image planes. The optical filter attenuates or partially blocks the light rays. The optical filter includes at least first and second filter regions having different opacity. The first and second filter regions are alignable with the lens system at different times to block different amounts of light rays associated with differing x-ray intensities that are transmitted at different times.

In accordance with at least one alternative embodiment, the optical filter includes a neutral density wheel having first and second sectors with differing thicknesses of opaque material deposited thereon to form the first and second filter regions. Optionally, the optical filter may include a circular filter having multiple sectors located adjacent one another. The sectors may have different opacities. Optionally, the optical filter may include filtered discs having at least two non-overlapping sectors of different opacity where the opacity is constant throughout each sector. As a further option, the optical filter may attenuate light passing there through to different degrees based on a rotational orientation of the optical filter with respect to the lens system.

In accordance with at least one embodiment, at least a portion of the first filter region is formed to be highly transparent to light rays and at least a portion of the second filter region is formed to have increasing opacity at progressively larger angular orientations of the optical filter with respect to a reference plane traversing the lens system. Optionally, the optical filter may be formed with a continuously varying opacity. The optical filter may variably attenuate the amount of light rays passed through the lens system based upon the position at which the optical filter is set relative to the lens system. Optionally, the optical filter may include a wheel located such that a sector of the wheel aligns with the lens system. The sector of the wheel aligned with the lens system represents one of the first and second filter regions. The wheel may have an opacity that continuously varies as a function of the angular orientation of the wheel with respect to the lens system.

Optionally, the optical filter may be formed with uniform opacity over discrete non-overlapping sectors where each discrete sector has a unique opacity that differs from other sectors by an amount based on an orientation of the optical filter with respect to the lens system. Optionally, the optical filter may include two filter wheels aligned with one another and having similar but opposite variations in opacity at progressively greater angular positions about the filter wheels.

In an alternative embodiment, the lens system may include forward and rear lens assemblies spaced apart from one another with the optical filter being positioned there between. Optionally, an iris may be located between the optical filter and the object plane with the iris including an aperture controlling a brightness of the light rays impingent upon the optical filter. The iris maintains a constant aperture at numerous x-ray intensities. Optionally, an electrical motor may be provided to adjust the position of the optical filter with respect to the lens system to automatically adjust attenuation of light rays by moving the optical filter between first and second positions to move the first filter region to an unused position and the second filter region to an operative position.

In accordance with at least one alternative embodiment, a medical x-ray system is provided having a support structure holding an x-ray source and receptor facing one another and aligned along a patient imaging axis. The x-ray source and receptor cooperate to obtain x-rays attenuated by a patient region of interest. The x-ray source may be controlled to vary an intensity of transmitted x-rays. The receptor converts x-rays to light rays representative of the patient region under examination, such that a brightness of the light rays varies based on the intensity of the x-rays received at the receptor. A processor processes the light rays to obtain x-ray images and a display displays processed x-ray images. A partially opaque member is provided to block a portion of the light rays to reduce a brightness of the light rays. The partially opaque member is provided with regions of different opacity.

In accordance with at least one embodiment, a motor assembly is provided for automatically moving the partially opaque member to vary the amount of attenuation of the brightness of the light rays. Optionally, means may be provided for shifting the partially opaque member from a highly opaque state to a lesser opaque state causing a reduction in an intensity of x-rays transmitted from the x-ray source until the average brightness of the light incident on the image sensor is reduced to the proper level.

Alternatively, a motor and gear assembly may be provided to rotate the partially opaque member between first and second angular positions to move a more opaque region of the partially opaque member into alignment with the light rays. Optionally, an assembly may be provided for moving the partially opaque member between an initial position at which light rays pass through a highly transparent portion of the partially opaque member to a final position at which a portion of the light rays are blocked by a highly opaque portion of the partially opaque member. Optionally certain regions of the partially opaque member may be provided with constant opacity. Optionally, regions of the partially opaque member may be provided with continuously varying opacity.

Figure 1:
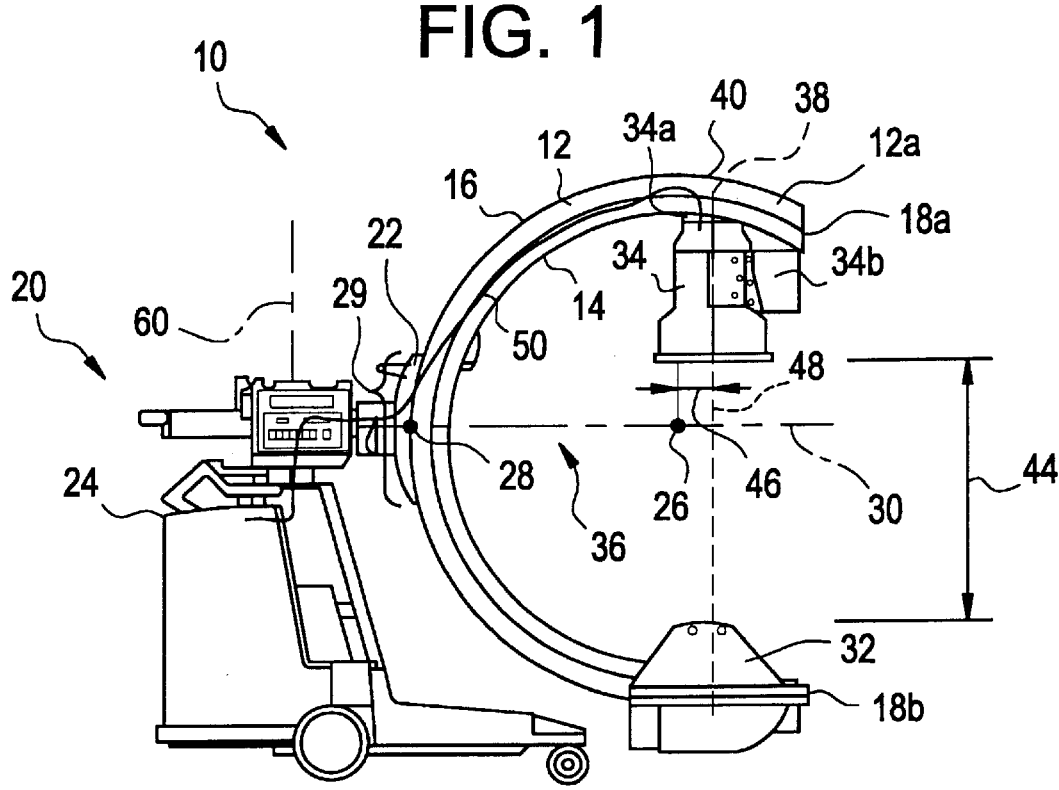
FIG. 1 illustrates a mobile x-ray imaging system formed in accordance with one embodiment of the present invention.

The foregoing summary, as well as the following detailed description of the preferred embodiments of the present invention, will be better understood when read in conjunction with the appended drawings. For the purpose of illustrating the preferred embodiments of the present invention, there is shown in the drawings, embodiments that are presently preferred. It should be understood, however, that the present invention is not limited to the arrangements and instrumentality shown in the attached drawings.

DETAILED DESCRIPTION OF THE INVENTION

An embodiment in accordance with the present invention is illustrated in FIG. 1 wherein is shown a C-arm X-ray apparatus, generally designated at 10. The apparatus 10 includes a C-arm 12 having inner and outer circumferences 14 and 16, respectively, and terminating in opposing upper and lower distal ends 18a and 18b. The C-arm 12 preferably has a uniformly circular C-shape, but may alternatively comprise any arc-shaped member.

The C-arm 12 is held in a suspended position by support means such as structure, generally designated at 20, which includes a support arm 22 mounted upon a wheeled base 24. The support arm 22 provides for rotational movement of the C-arm 12 about an axis of lateral rotation 30, either by a bearing assembly between the support arm 22 and the C-arm 12, or by the support 22 itself being rotatably mounted with respect to the base 24.

The wheeled base 24 enables transport of the C-arm 12 from a first location to a second location. As such, the wheels of the base operate as transporting means coupled to the support structure 20 for transporting the support arm 22 and the C-arm 12 from a first location to a second location. It may be preferable to move X-ray equipment from one room to another. The mobile nature of the apparatus 10 as provided by the wheeled base 24 offers increased access by patients in many different rooms of a hospital, for example.

The support arm 22 is slidably mounted to the outer circumference 16 of the C-arm 12 and the support structure 20 includes structure and mechanisms necessary to enable selective, sliding orbital motion of the C-arm about an axis of orbital rotation 26 to a selected position. The axis 26 preferably coincides with a center of curvature of the C-arm 12 and with the axis of lateral rotation 30. It will be appreciated that the sliding orbital motion causes the C-arm 12 to move through various sliding points of attachment 28. to the support arm 22. The support structure 20 further includes mechanisms for laterally rotating the support arm 22 selectable amounts about an axis of lateral rotation 30 to a selected lateral position. The combination of sliding orbital motion and lateral rotation enables manipulation of the C-arm in two degrees of freedom, i.e. about two perpendicular axes. This provides a kind of spherical quality to the movability of the C-arm 12—the sliding orbital motion and lateral rotation enable an X-ray source 32 coupled to the C-arm to be moved to substantially any latitude/longitude point on a lower hemisphere of an imaginary sphere about which the C-arm is moveable.

The apparatus 10 includes an X-ray source 32 and an image receptor 34 as known generally in the X-ray diagnostic art, mounted upon opposing locations, respectively, on the C-arm 12. The X-ray source 32 and the image receptor 34 may be referred to collectively as the X-ray source/image receptor 32/34. The image receptor 34 can be an image intensifier or the like. The orbital and laterally rotational manipulation of the C-arm enables selective positioning of the X-ray source/image receptor 32/34 with respect to the width and length of a patient located within interior free space 36 of the C-arm 12. The sliding orbital movement of the C-arm causes the X-ray source/image receptor 32/34 to move along respective arcuate movement paths. The image receptor 34 is preferably secured to the inner circumference 14 of the C-arm 12 and the X-ray source 32 may also be secured to said inner circumference 14, the significance of which will be described below.

Figure 2:
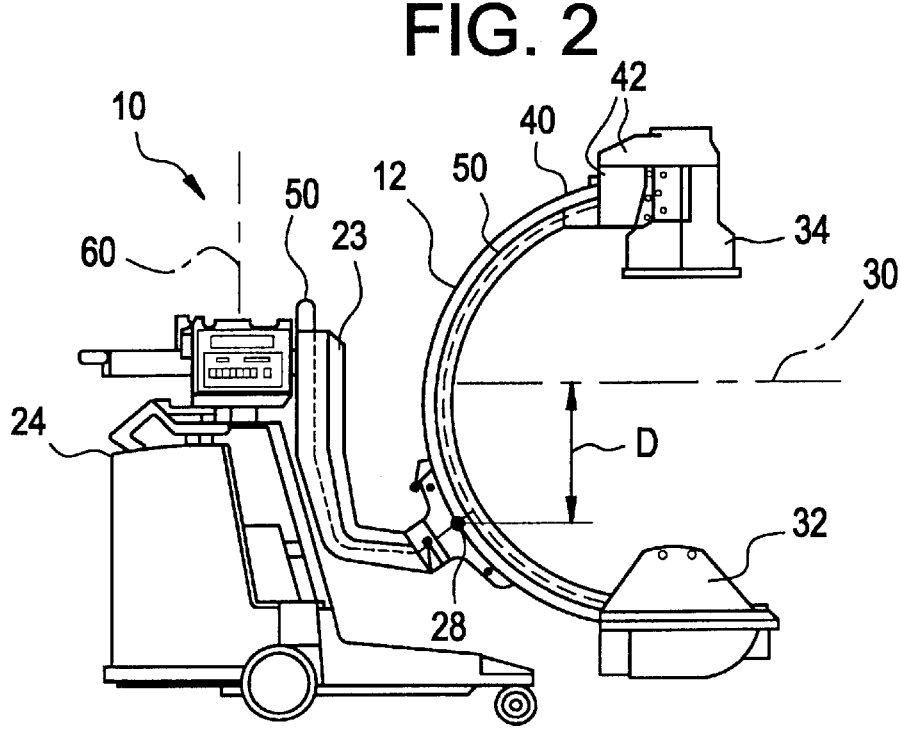
FIG. 2 illustrates an x-ray imaging system formed in accordance with an alternative embodiment of the present invention.

Another C-arm support structure, exemplified in FIG. 2, includes a downwardly-extending L-arm 23 such that its point of attachment 28 with the C-arm 12 resides a distance D away from the axis of lateral rotation 30. The image receptor 34 on the C-arms are mounted and positioned in such a way as to encumber a back convex portion 40 of the C-arm 12, as shown by encumbering portions 42 in FIG. 2, thereby preventing the support arm 23 from slidably attaching to that portion 12a of the C-arm. In order to achieve complete horizontal positioning of the image receptor 34, the L-arm was developed to attach to the C-arm the point of attachment 28 below the axis of lateral rotation 30, thus permitting the C-arm 12 to slide the image receptor 34 to at least a horizontal orientation. This introduces an eccentric lateral moment arm D upon lateral rotation of the C-arm 12 about the axis 30. This typically requires lateral rotation of the C-arm 12 about the axis 30 to be electrically powered to overcome the torque that results from the imbalance.

Figure 3:
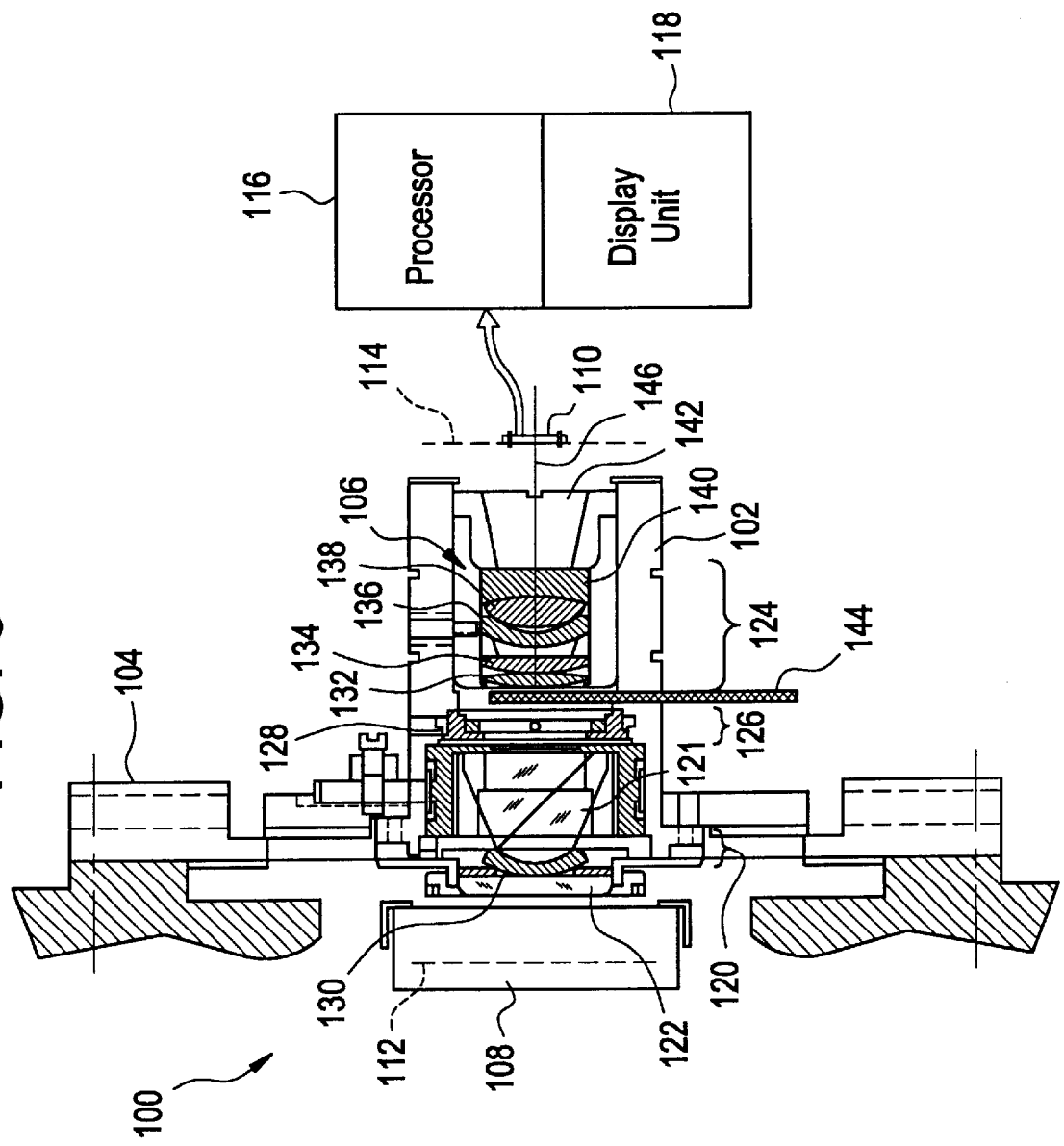
FIG. 3 illustrates a side sectional view of an optical camera assembly formed in accordance with an embodiment of the present invention.

FIG. 3 illustrates a side sectional view of a camera apparatus 100 included within the image receptor 32. The camera apparatus 100 includes a housing 102 mounted to a lateral bracket 104. The housing 102 and bracket 104 cooperate to securely locate camera optics 106 at a desired location with respect to an image intensifier 108 and a light sensor 110 (e.g., a CCD). The camera optics 106 are located between an object plane 112 and an image plane 114. The image intensifier 108 is located to direct light rays onto the object plane 112 where such light rays are representative of an x-ray image detected by the receptor 32. The light sensor 110 is located proximate the image plane 114 and operates to convert light rays focused on or substantially near the image plane 114 into data that is subsequently processed by a processor 116 and displayed by a display unit 118.

The camera apparatus 100 includes a leaded glass cover 122 located proximate the object plane 112. The glass cover 122 blocks x-rays from reaching the light sensor 110, while permitting light rays to pass therethrough. The camera optics 106 include a forward lens assembly and optical prism 121 (pechan prism) located proximate the glass cover 122 and a rear lens assembly 124 located proximate an opposite end of the camera apparatus 100. The prism 121 enables the forward and rear lens assemblies 120 and 124 to be closely spaced. The rear lens assembly 124 is located proximate the image plane 114. The forward lens assembly and optical prism 121 collimates light ray traces passing through the glass cover 122 and provides a compacted path length for the near-columnar light to travel, while the rear lens assembly 124 reconverges such collimated light ray traces. The forward and rear lens assembly 120 and 124 cooperate to focus ray traces from the object plane 112 onto the image plane 114.

The camera optics 106 further include optics components 126 that may be used to effect a variety of operations. An iris 128 is provided having an opening therethrough that is adjustable in diameter to control a brightness of light passing therethrough.

The forward lens assembly 120 may be formed in a variety of manners. By way of example only, the forward lens assembly 120 may include a complex convex lens 130 having forward and rear portions. The rear lens assembly 124 may also include a variety of lens configurations. By way of example only, the rear lens assembly 124 may include first through fifth lenses 132, 134, 136, 138 and 140 arranged adjacent one another as shown with various combinations of convex and concave surfaces. A rear structure 142 isolates the rear end of the camera apparatus 100 to protect the camera optics 106 from environmental elements while permitting light rays to pass therethrough.

The camera optics 106 further include a filter member 144 positioned with a portion of the filter member 144 spanning the opening between the forward and rear lens assemblies 120 and 124. The filter member 144 is partially opaque to attenuate light rays passing from the forward lens assembly 120 to the rear lens assembly 124. The filter member 144 has differing amounts of opaqueness at different positions upon the filter member 144. The filter member 144 is moved to different positions, while at least a portion of the filter member 144 remains between the forward and rear lens assemblies 120 and 124 in order to align desired regions of differing opacity along the line of sight 146 extending between the forward and rear lens assemblies 120 and 124.

Figure 4:
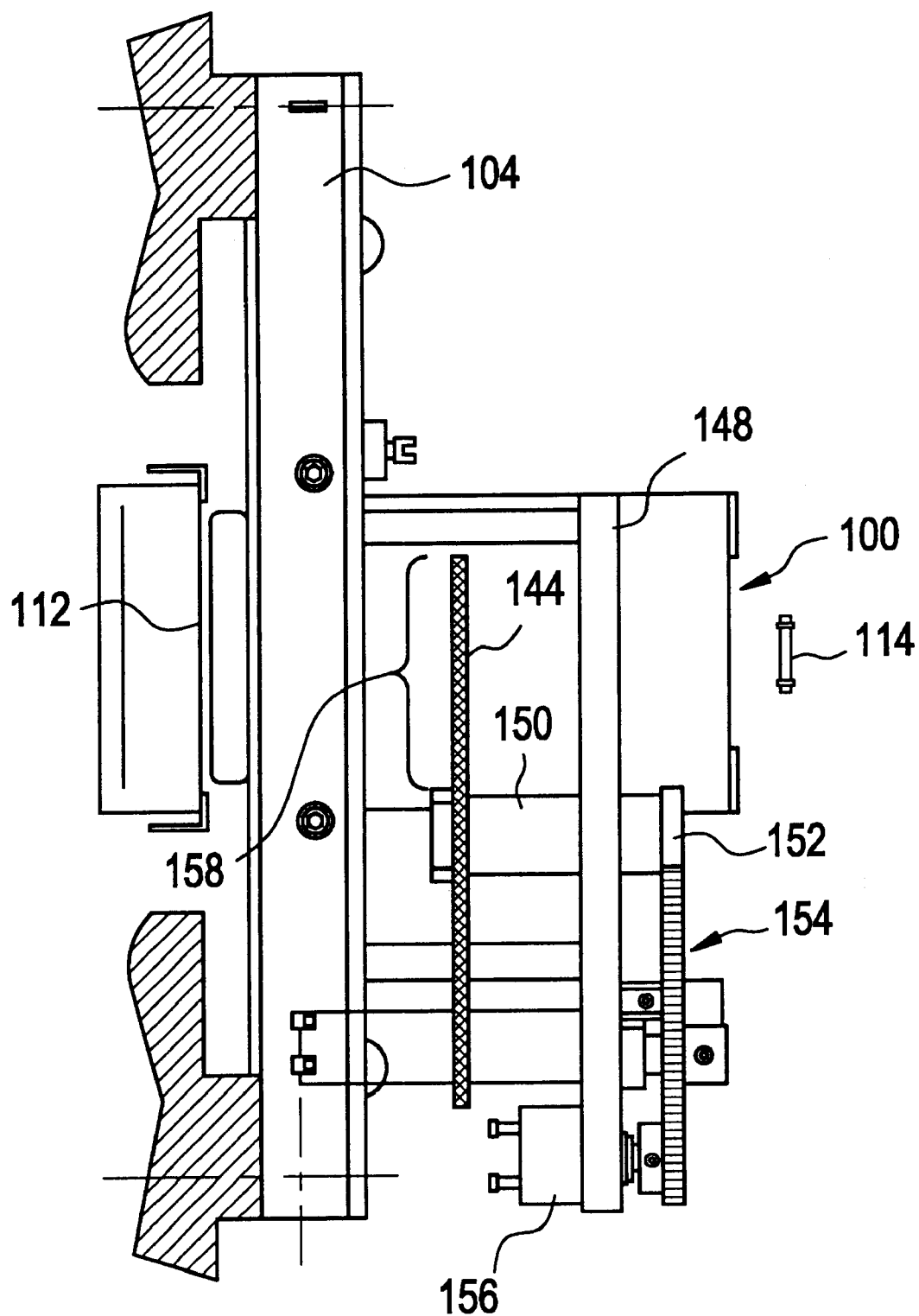
FIG. 4 illustrates a side view of a portion of an optical camera apparatus formed in accordance with an embodiment of the present invention.
Figure 5:
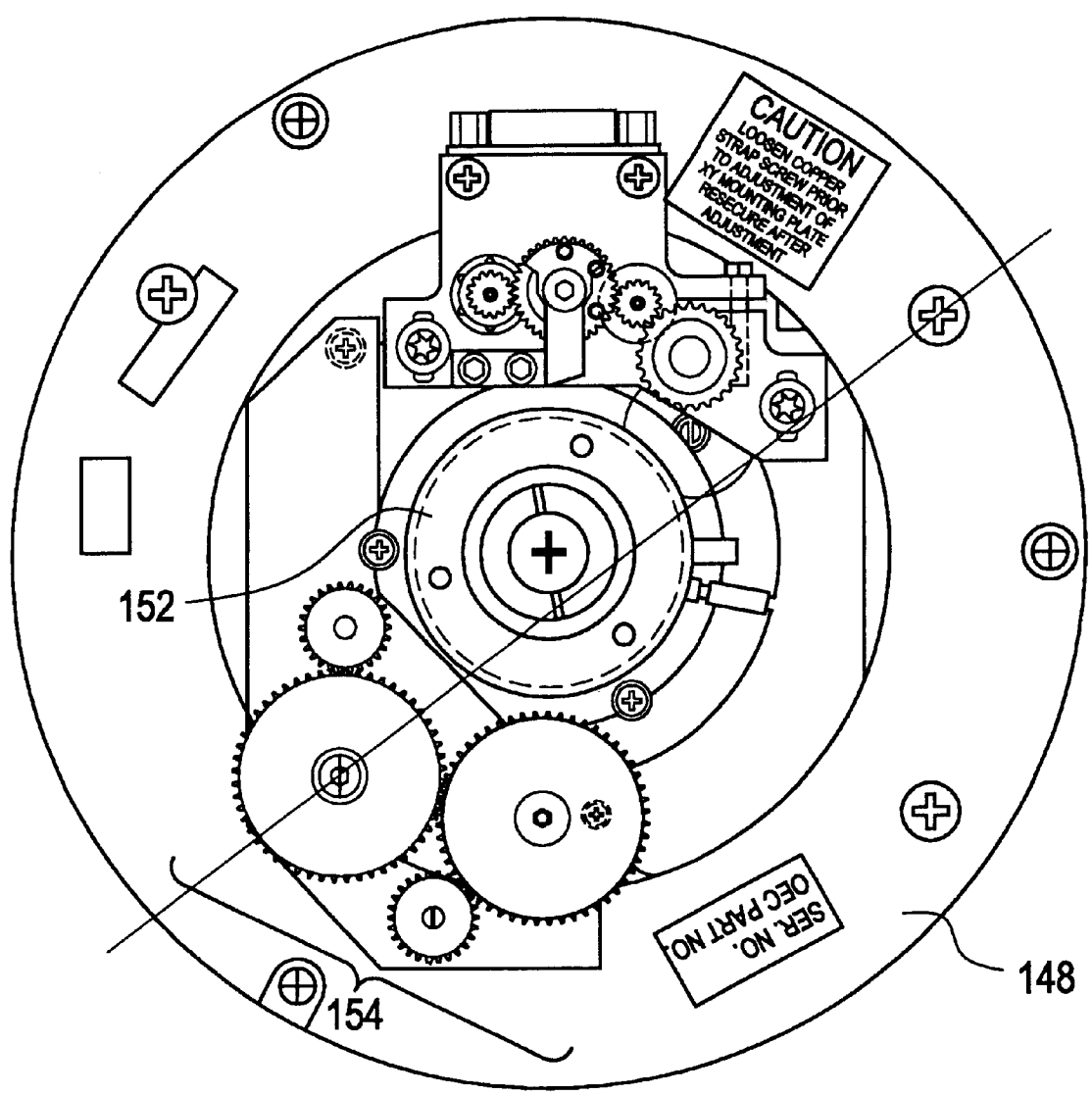
FIG. 5 illustrates a front view of a portion of the optical and mechanical camera apparatus formed in accordance with an embodiment of the present invention.

FIG. 4 illustrates the filter member 144 in more detail. A bracket 148 mounts the filter member 144 to the bracket 104 and camera apparatus 100. The bracket 148 includes a rotatable support pin 150 having the filter member 144 secured to one end thereof. An opposite end of the support pin 150 is secured to a gear 152 that is part of a larger gear assembly 154 that is driven by a motor 156. The motor 156 is controlled by the processor 116 (or a separate and distinct control processor not shown). The motor rotates the filter member 144 through the gear assembly 154 in order to position a portion 158 of the filter member 144 between the object and image planes 112 and 114. The portion so aligned is considered the active portion. FIG. 5 illustrates a front view of the gear assembly 154 in more detail.

Figure 6:
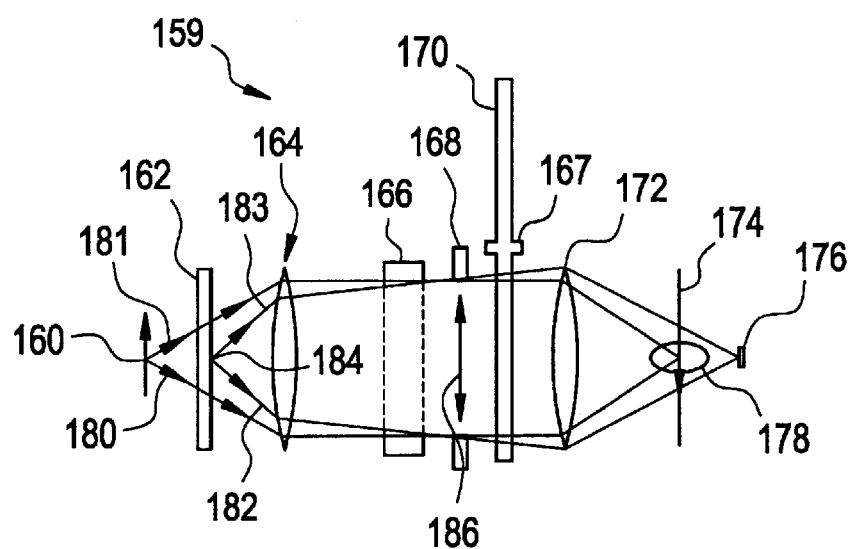
FIG. 6 illustrates a graphical representation of an optical assembly formed in accordance with an embodiment of the present invention.

FIG. 6 illustrates graphically one embodiment of a camera optics 159. An object plane 160 and an image plane 174 are located on opposite sides of the camera optics 159. A leaded glass cover 162 is located proximate a forward lens assembly 120 which is in turn located proximate optics components 166 and iris 168. A light attenuator 170 is provided between the forward lens assembly 164 and rear lens assembly 172. Optionally, the iris 168 may be removed and/or the optics components 166 may be removed. The optics components 166, iris 168 and light attenuator 170 may be reordered. Light rays 180 and 181 from an object at the object plane 160 are collimated by the forward lens assembly 164 and re-converged by the rear lens assembly 172 to be focused at the image plane 174. Light rays 182 and 183 from a blemish 184 on the glass cover 162 are collimated and re-converged by the forward and rear assemblies 164 and 172, respectively, to be focused at a point 176 beyond the image plane 174. The point 176 at which the blemish 184 is focused is outside of the focus region 178 surrounding the object plane 174. The focus region 178 is maintained small enough to exclude the focus point 178 by maintaining the diameter of the aperture through the iris 168 relatively large. Hence, the blemish 184 is not adequately in focus at the image plane 174 to be detected as an artifact by the light sensor, nor displayed as an artifact in the x-ray image.

Figure 8:
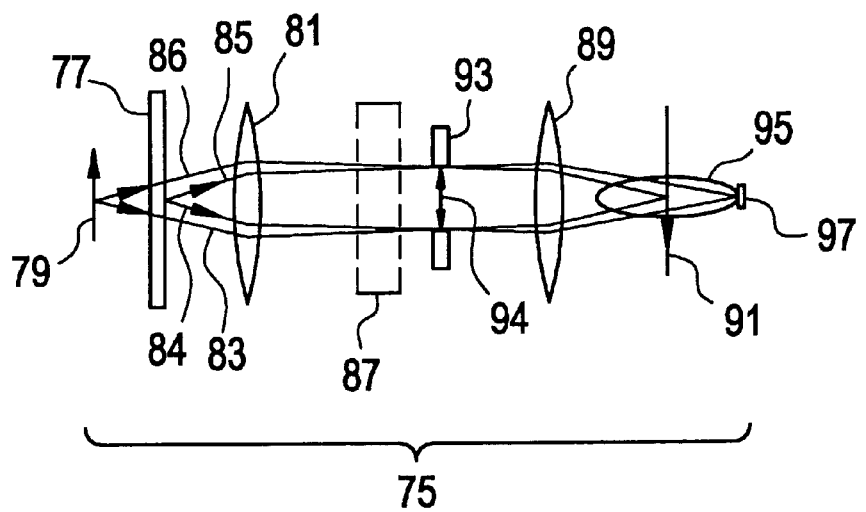
FIG. 8 illustrates a graphical representation of a conventional optical camera apparatus.

As is apparent from a comparison of FIGS. 6 and 8, for high intensity x-ray shots, the diameter 186 of the opening through iris 168 is substantially larger than the diameter 94 of the opening through iris 93 as used in conventional camera optics 75. The diameter 186 of the opening through the iris 168 may remain constant over a wide range of x-ray intensities. As the light attenuator 170 is adjusted to increase the degree to which the light is attenuated, the system will automatically respond by increasing x-ray intensity per feedback obtained by monitoring the average amount of light intensity at the light sensor located at the image plane 174. Similarly, as the light attenuator 170 is adjusted to decrease the degree to which the light is attenuated, the x-ray intensity is decreased.

Figure 7:
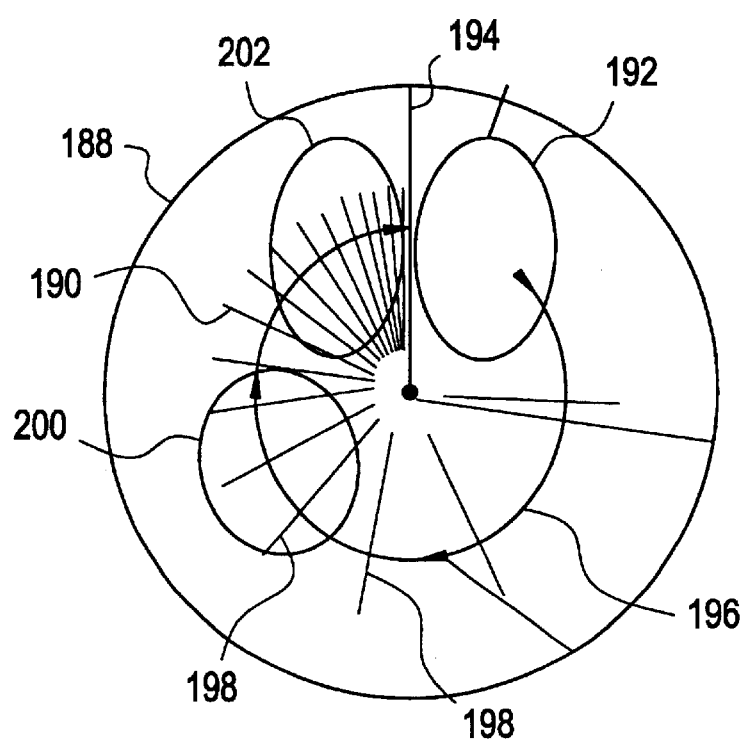
FIG. 7 illustrates a graphical representation of an optical filter formed in accordance with an embodiment of the present invention.

FIG. 7 illustrates a neutral density wheel 188 that, in accordance with one embodiment, may be utilized as a light attenuator 170. The neutral density wheel 188 is circular and is positioned to rotate about a filter axis that is parallel to an imaging axis extending through the camera optics 159. The filter axis is spaced apart from the imaging axis by a distance based on the radius of the neutral density wheel 188. For example, filter axis may be spaced slightly outside the view of the camera optics 159 such that a sector of the neutral density wheel 188 extends through and covers the active viewing area between the forward and rear lens assemblies 164 and 172.

The neutral density wheel 188 may be formed from a transparent material, such as glass and the like, that is coated with an opaque material. The opaque material may be coated on the neutral density wheel 188 in a progressively thicker coating to vary the amount of opacity. In the example of FIG. 7, the opaque coating becomes thicker (and thus the amount of attenuation increases) as it moves in the clockwise direction around the neutral density wheel 188. Alternatively, the neutral density wheel 188 may be coated in step-wise even sections to form non-overlapping discrete sections of equal opacity. Alternatively, the neutral density wheel 188 may be formed from a mosaic of individual pieces that are secured to one another. Each mosaic piece may have an even coating thereon.

In FIG. 7, radial lines 190 and 198 graphically illustrate the opacity. Hence, in region 192 with no radial lines, the opaque coating is either non-existent or very thin to render the neutral density filter 188 substantially transparent to light. At progressively greater angles along circular arc 196 away from a reference mark 194, the opaque material is coated thicker. For instance, the radial lines 198 proximate region 200 are spaced relatively far apart, as compared to the radial lines 190 in region 202. This illustrates that the neutral density filter 188 is more opaque in region 202 than in region 200. Similarly, region 200 is more opaque than region 192.

The thickness of the opaque material may be varied continuously or in very small narrow step-wise sectors to afford fine resolution. The use of fine resolution enables the x-ray intensity to similarly be varied in small or fine steps to achieve close control over the amount of x-rays, to which a patient is exposed. For example, the neutral density wheel 188 may be rotated by a small amount to slightly adjust the attenuation. Once the wheel 188 is rotated, the system then adjusts the intensity of the x-rays based on the new position of the wheel 188.

A sensor, such as a potentiometer, is provided on one of the wheels 188, the gear assembly 154 and the motor 156. The sensor may sense the position of the axle of the wheel 188. The sensor affords precise control over the wheel 188 position. The processor senses the axle position and drives the motor 156 until the wheel 188 is properly oriented.

Figure 9:
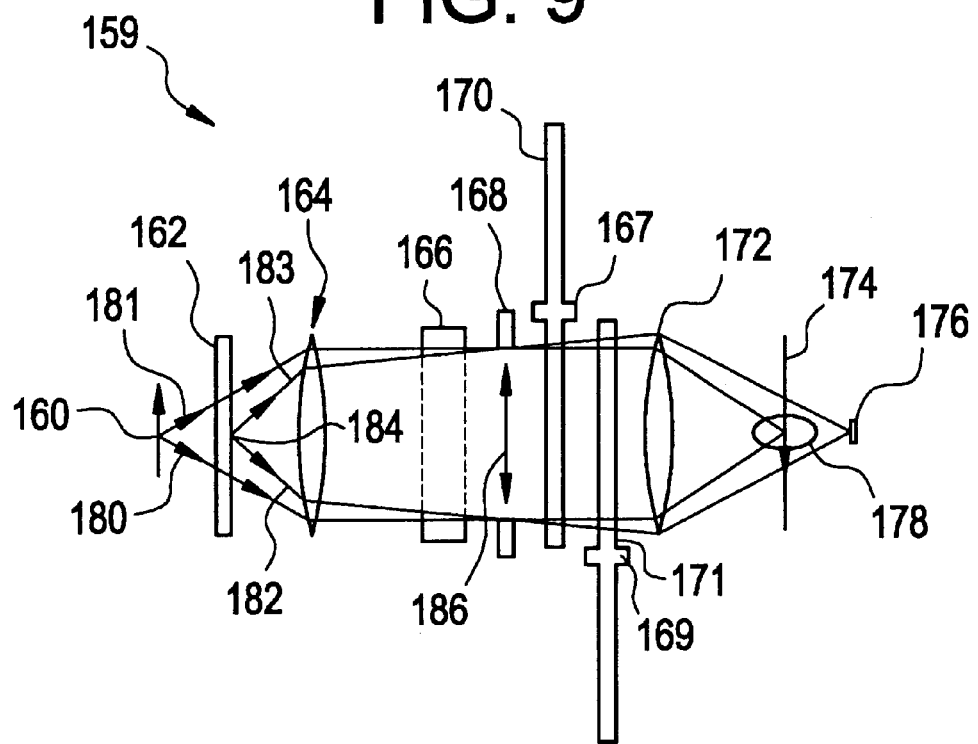
FIG. 9 illustrates a graphical representation of an alternative optical filter formed in accordance with an embodiment of the present invention.

Optionally, multiple light attenuators may be utilized. By way of example only, FIG. 9 illustrates a second light attenuator 171 located adjacent and aligned parallel to the light attenuator 170. The rotational axes 167 and 169 of the light attenuators 170 and 171, respectively, may be along different axes (as shown). Alternatively, the light attenuators 170 and 171 may be formed directly in line with one another to rotate about a common axis, such as axis 167. Optionally, a single motor may drive both light attenuators 170 and 171. Alternatively, different motors may drive light attenuators 170 and 171.

The light attenuators 170 and 171 are coated with opaque material, the thickness of which varies in opposite directions from one another. Hence, when light attenuators 170 and 171 overlap one another in the viewing area between the forward and rear lens assemblies 164 and 172, the opacity is substantially even across the viewing area even though the opacity varies continuously on each individual light attenuator 170 and 171. By way of example, in the viewing area, the attenuation caused by the light attenuator 170 may increase while moving in a clock-wise direction around the light attenuator 170, whereas the attenuation caused by the light attenuator 171 may increase while moving in a counter clock-wise direction around the light attenuator 171. The composite attenuation caused by both light attenuators 170 and 171 is relatively even across the viewing area.

The neutral density wheel 188 is described as circular with continuous or stepped sectors of opaque material coated thereon. However, other shapes may be used as well. Also, the opaque material need not be a coating. Also, the opaque material need not be sector shaped. For instance, the light attenuator 170 may be rectangular, octagonal, square, triangular, pentagonal and the like. The light attenuator need only be divided into two or more regions of differing opacity. If rectangular, the light attenuator 170 may be formed with opaque regions shaped as strips extending from the top to the bottom of the light attenuator 170. If so structure, the light attenuator 170 would then be slid laterally in a direction transverse to the imaging axis in order to move a region of desired opacity into alignment with the forward and rear lens assemblies 164 and 172.

While the invention has been described with reference to alternative embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. In a medical x-ray imaging system, an electronic video camera focusing light rays from an object plane proximate an image intensifier onto an image plane proximate a light sensor, said electronic video camera comprising:

an object plane receiving light rays representative of a patient image;

a lens system, located between the object plane and the image plane, focusing said light rays from said object plane onto said image plane;

an optical filter, located between the object and image planes, partially blocking said light rays, said optical filter including at least first and second filter regions having different opacity, said first and second filter regions being alignable with said lens system at different times to block differing first and second amounts of light rays, respectively, associated with differing first and second x-ray amounts transmitted at different times.

2. The electronic video camera of claim 1, wherein said optical filter includes a neutral density wheel having first and second sectors with differing thicknesses of opaque material deposited thereon to form said first and second filter regions.

3. The electronic video camera of claim 1, wherein said optical filter includes a circular filter having multiple sectors located adjacent one another, said sectors having different opacities.

4. The electronic video camera of claim 1, wherein said optical filter includes a filter disc having at least two non-overlapping sectors of differing opacity, and wherein opacity is constant throughout each sector.

5. The electronic video camera of claim 1, wherein said optical filter attenuates light passing there through to differing degrees based on a rotational orientation of said optical filter with respect to said lens system.

6. The electronic video camera of claim 1, wherein at least a portion of said first filter region is highly transparent to light rays and at least a portion of said second filter region has increasing opacity at progressively larger angular orientations of said optical filter with respect to a reference plane traversing said lens system.

7. The electronic video camera of claim 1, wherein said optical filter is formed with a continuously varying opacity across said optical filter, said optical filter varying an amount of light rays passed through said lens system based upon a position of said optical filter with respect to said lens system.

8. The electronic video camera of claim 1, wherein said optical filter includes a wheel located such that a sector of said wheel aligns with said lens system, said sector aligned with said lens system representing one of said first and second filter regions, said wheel having continuously varying opacity as a function of an angular orientation of said wheel with respect to said lens system.

9. The electronic video camera of claim 1, wherein said optical filter has uniform opacity over discrete non-overlapping sectors of said wheel, each sector having an opacity differing from other sectors by an amount based on an orientation of said optical filter with respect to said lens system.

10. The electronic video camera of claim 1, wherein said optical filter includes two filter wheels aligned with one another and having similar and opposite variations in opacity at progressively greater angular positions about said filter wheels.

11. The electronic video camera of claim 1, wherein said lens system includes rear and forward lens assemblies spaced apart from one another, said optical filter being positioned between said rear and forward lens assemblies.

12. The electronic video camera of claim 1, further comprising an iris located between said optical filter and the object plane, said iris including an aperture controlling a brightness of light rays impinging upon said optical filter, said iris maintaining a constant aperture when receiving said first and second different amounts of light rays at said different times.

13. The electronic video camera of claim 1, further comprising an electric motor adjusting a position of said optical filter with respect to said lens system to automatically adjust attenuation of light rays by moving said optical filter between first and second positions to move to said first filter region to an unused position and said second filter region to an operative position.

14. A medical x-ray system comprising:
- a support structure holding an x-ray source and receptor facing one another and aligned along a patient imaging axis;
- said x-ray source and receptor cooperating to obtain x-ray patterns attenuated by a patient, said x-ray source varying an intensity of x-rays transmitted;
- said receptor converting x-rays to light rays representative of a patient region, a brightness of said light rays varying based on an intensity of the x-rays;
- a processor processing said light rays to obtain x-ray images;
- a display for displaying said x-ray images;
- a partially opaque member blocking a portion of said light rays to reduce a brightness of said light rays, said partially opaque member having regions with different opacities; and
- motor assembly for moving said partially opaque member to vary reduction of the brightness of said light rays.

15. The system of claim 14, wherein said partially opaque member has regions varying in opacity from one another.

16. The system of claim 14, wherein said partially opaque member has regions varying in opacity from one another, at least one region having constant opacity.

17. The system of claim 14, wherein said partially opaque member has regions varying in opacity from one another, at least one region having continuously varying opacity.

18. A medical x-ray system comprising:
- a support structure holding an x-ray source and receptor facing one another and aligned along a patient imaging axis;
- said x-ray source and receptor cooperating to obtain x-ray patterns attenuated by a patient, said x-ray source varying an intensity of x-rays transmitted;
- said receptor converting x-rays to light rays representative of a patient region, a brightness of said light rays varying based on an intensity of the x-rays;
- a processor processing said light rays to obtain x-ray images;
- a display for displaying said x-ray images;
- a partially opaque member blocking a portion of said light rays to reduce a brightness of said light rays, said partially opaque member having regions with different opacities; and
- means for shifting said partially opaque member from a highly opaque state to a lesser opaque state in order to cause a reduction in an intensity of x-rays transmitted from said x-ray source via automatic feedback response of the x-ray system.

19. A medical x-ray system comprising:
- a support structure holding an x-ray source and receptor facing one another and aligned along a patient imaging axis;
- said x-ray source and receptor cooperating to obtain x-ray patterns attenuated by a patient, said x-ray source varying an intensity of x-rays transmitted;
- said receptor converting x-rays to light rays representative of a patient region, a brightness of said light rays varying based on an intensity of the x-rays;
- a processor processing said light rays to obtain x-ray images;
- a display for displaying said x-ray images;
- a partially opaque member blocking a portion of said light rays to reduce a brightness of said light rays, said partially opaque member having regions with different opacities; and
- a motor and gear assembly rotating said partially opaque member between first and second angular positions to move a more opaque region of said partially opaque member into alignment with said light rays.

20. A medical x-ray system comprising:
- a support structure holding an x-ray source and receptor facing one another and aligned along a patient imaging axis;
- said x-ray source and receptor cooperating to obtain x-ray patterns attenuated by a patient, said x-ray source varying an intensity of x-rays transmitted;
- said receptor converting x-rays to light rays representative of a patient region, a brightness of said light rays varying based on an intensity of the x-rays;
- a processor processing said light rays to obtain x-ray images;
- a display for displaying said x-ray images;
- a partially opaque member blocking a portion of said light rays to reduce a brightness of said light rays, said partially opaque member having regions with different opacities; and
- an assembly for moving said partially opaque member between an initial position at which said light rays pass through a highly transparent portion of said partially opaque member and a final position at which a portion of said light rays are blocked by a highly opaque portion of said partially opaque member.

* * * * *